United States Patent [19]

Drake et al.

[11] Patent Number: 4,851,225

[45] Date of Patent: Jul. 25, 1989

[54] MATERIAL DISPENSERS

[75] Inventors: Cyril F. Drake, Harlow; Alfred J. Arch, Ongar, both of Great Britain

[73] Assignee: STC PLC, London, England

[21] Appl. No.: 34,703

[22] Filed: Apr. 6, 1987

[30] Foreign Application Priority Data

Apr. 16, 1986 [GB] United Kingdom ............... 8609310

[51] Int. Cl.⁴ ........................................... A61K 31/015
[52] U.S. Cl. .................................... 424/438; 424/426; 514/964
[58] Field of Search ................. 424/438, 426; 514/964

[56] References Cited

U.S. PATENT DOCUMENTS

| 4,350,675 | 9/1982 | Drake ..................................... 424/9 |
| 4,407,786 | 10/1983 | Drake et al. ......................... 424/426 |
| 4,449,981 | 5/1984 | Drake et al. ......................... 424/426 |
| 4,662,879 | 5/1987 | Drake et al. ......................... 424/438 |

FOREIGN PATENT DOCUMENTS

| 0449029 | 3/1972 | Australia ............................ 424/438 |
| 1146864 | 5/1983 | Canada ............................... 424/438 |
| 0164927 | 12/1985 | European Pat. Off. ............ 424/438 |
| 2077585 | 12/1981 | United Kingdom ................ 424/426 |
| 2077586 | 12/1981 | United Kingdom ................ 424/426 |
| 2079152 | 1/1982 | United Kingdom ................ 424/426 |

Primary Examiner—Thurman K. Page
Assistant Examiner—P. J. Ryan
Attorney, Agent, or Firm—Lee & Smith

[57] ABSTRACT

A dispenser for use, for instance, as a rumen bolus is a generally cylindrical container (1) for material to be dispersed into the digestive tracts, etc. of a ruminant. The container has a closure (3) held in place by a controlled release glass (CRG) member (5). When this member is dissolved, the closure (3) comes out and the contents are released. The cylindrical container can be formed by a hole in a larger member which has several such holes so that different materials can be released, or materials released at different times.

Variants include stacked arrangements in which several dispenser compartments are coupled so that as one is emptied a CRG member is dissolved to release material in the next compartment.

In some cases the CRG member acts both as the release device, and as the closure for its compartment, and in others it also acts as a means of linking a number of detachable sections.

10 Claims, 7 Drawing Sheets

MATERIAL DISPENSERS

BACKGROUND OF THE INVENTION

The invention relates to dispensers, and especially to the intra-ruminal delivery of veterinary materials to ruminant animals, and to rumen boluses for effecting such delivery.

An object of this invention is to provide improved forms of dispensers suitable for use, inter alia, as rumen boluses.

SUMMARY OF THE INVENTION

According to the invention, there is provided a dispenser for dispensing material into a fluid medium, which dispenser when in use is located in the fluid medium into which the material is to be dispensed, the dispenser including a container for the material to be dispensed, a closure for the container, and a retainer which holds the closure in place, the retainer being made of a controlled release glass (CRG) material, wherein in use the dispenser is immersed in the fluid medium so that the CRG retainer is subjected to the dissolving action of the fluid, so that the CRG dissolves in the fluid medium, whereby the retainer is rendered ineffective after a period which depends on the characteristics of the CRG retainer, so that the closure is released to cause the material to be dispensed to be released to the fluid medium.

BRIEF DESCRIPTION OF THE DRAWINGS

Embodiments of the invention will now be described with reference to the accompanying drawings, in which.

DESCRIPTION OF PREFERRED EMBODIMENTS OF THE INVENTION

Figure 1:
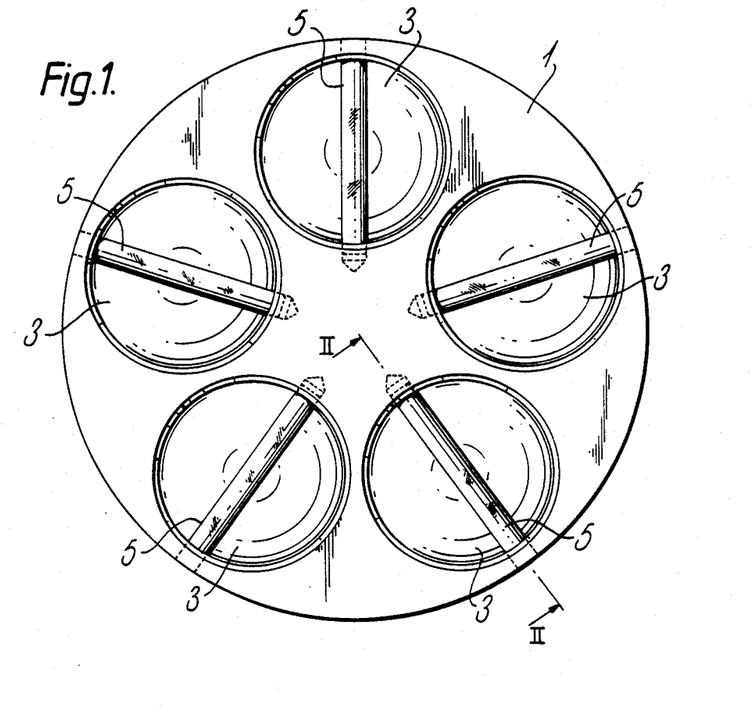
FIG. 1 is a plan view of a multi-dispenser pack.
Figure 2:
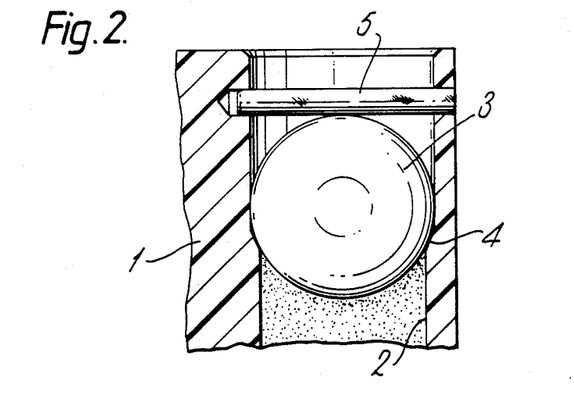
FIG. 2 is a section along the line X—X of one of the dispensers of the pack of FIG. 1.

FIGS. 1 and 2 show a first form of multi-dispenser pack in which for each individual dispenser or capsule there is a separate closure member and release member. This arrangement is a cylindrical member 1 of a plastics material such as an acrylic material with five holes such as 2 in it, each such hole accommodating a material to be released. In the case of a pack for insertion into the rumen of a cow this material could be a nutrient or a material of medicinal value.

Each hole is closed by a rubber or plastics ball 3 resting on a bevelled region 4 of a wall of its hole. This ball is retained in place by a rod or tube 5 of a controlled release glass (CRG). To give scale, the CRG rod in one example was 13 mm long.

When the bolus formed by the pack shown in FIGS. 1 and 2 is in the rumen, the fluids therein dissolve the CRG rods, and when such a rod is dissolved sufficiently, its ball is released and the material in the appropriate hole is released into the animal's rumen. The CRG rods can have different release times and the various holes or capsules can contain different materials.

The CRG materials used for the rods or tubes are made for materials listed in Table 1, which appears near the end of the specification. This table shows starting points for five different CRG materials.

For each example the materials after being mixed are melted in an electrical resistance furnace in air, at a temperature of about 1100° C. for 30 mins. The resulting material is then cast and annealed. Table 2, also near the end of the specification, indicates the compositions of the resulting materials, with the release characteristics. The numbered compositions in Table 2 correspond to the batches in Table 1.

Figure 3:
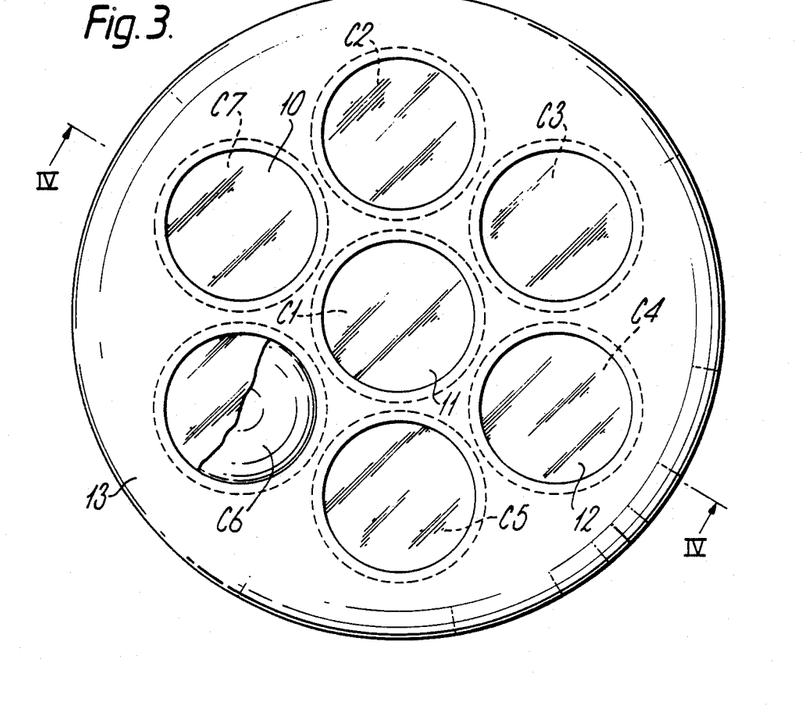
FIG. 3 is a plan view of another multi-dispenser pack.
Figure 4:
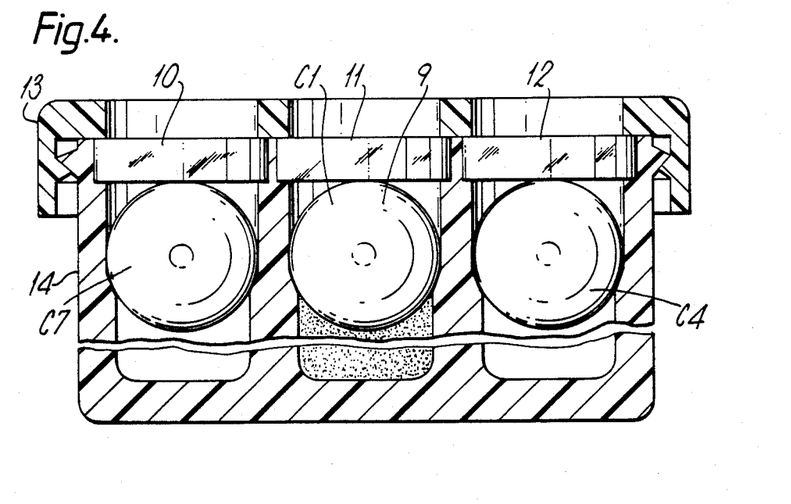
FIG. 4 is a section along the line X—X of three of the dispensers of the pack of FIG. 2.

The arrangement of FIGS. 3 and 4 is similar in essence to that of FIGS. 1 and 2, but has seven capsules, listed as C1 to C7. These are of similar dimensions to the holes in FIGS. 1 and 2. In this case the balls such as 9 are held in place by discs such as 10, 11, 12 of CRG. Each of these discs is received by shoulders on the inner surfaces of the holes, and the discs are held in place by a polythene cap 13, which is a snap-on fit over the body 14 of acrylic material. Naturally where the arrangement is used in a living creature such as a cow, the materials used are harmless and non-toxic.

We now come to a number of arrangements which follow the principles of the above-described arrangements, but with slightly different release mechanisms. In addition, these arrangements include a number of capsules with successive release, i.e. a pulse release arrangement.

Figure 5:
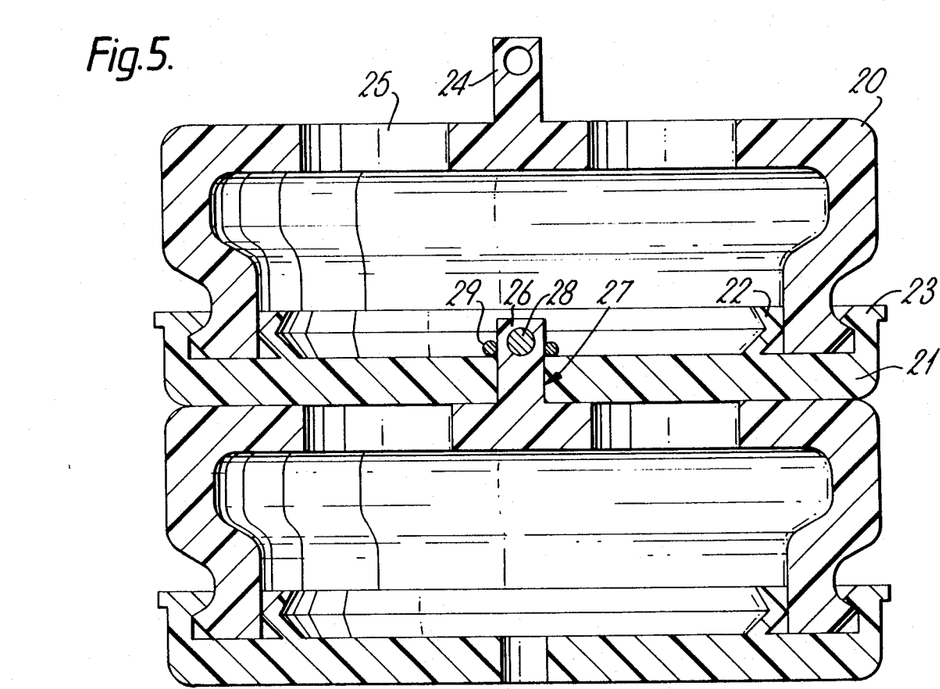
FIG. 5 is a section of an assembly of two dispensers so arranged that they can be released sequentially.

In FIG. 5 we see an assembly of two similar capsules, each of which includes a cap portion 20 of an acrylic plastics and a base portion 21 of polythene. The two fit together by spring rings 22, 23 on the base 21, into which the rim of the cap fits. On the outer surface of the cap there is a centrally located lug 24 with a hole in it, surrounded by holes 25, four in number in this case. Such capsules have outside diameters of about 35 mm.

The lug 26 on the lower cap projects through a hole 27 in the bottom of the base portion, and is held there by a rod 28 of CRG, under which is a O ring 29. When the material in the upper capsule 6 has been used up, the fluid in which the assembly is located gets to the rod 28, which is dissolved. When this action has gone far enough, the two capsules separate, and the contents of the lower capsule can escape.

Such an arrangement can consist of a number of similar capsules stacked together, i.e. with another capsule (not shown) below the lower capsule of FIG. 5.

With the assembly as shown, as soon as the device is installed, in the rumen of a cow of sheep in the present case, the contents of the upper capsule commence to escape by solution in the "ambient" fluid. However, if it is desired to have a delay before the contents of the first capsule are used, then the holes 25 could initially each be filled with a disc of CRG.

FIGS. 6-11 show alternative ways of securing two capsules, each otherwise similar to the capsules of FIG.

5, together. Here also a larger number can be stacked together.

Figure 6:
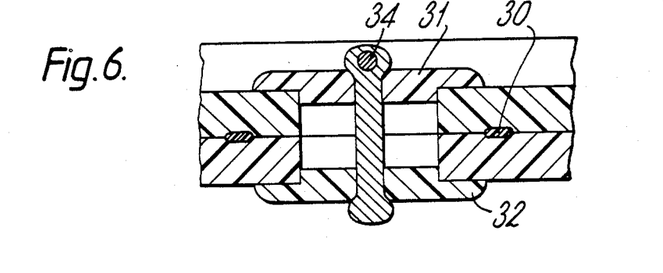
FIGS. 6 to 11 are partial sections showing different ways to secure dispensers such as shown in FIG. 2 for sequential release.

In FIG. 6 the lower portion of one capsule and the upper portion of the other are separated by a sealing ring 30, and are fastened together by two washers 31, 32, with a dumb-bell shaped rubber or the like rod extending through the washers. The upper end of this rod has a CRG rod or tube 34 forced through it. When this CRG rod or tube is exposed to fluid, it is dissolved away, so that the distorted end of the rod 34 returns to its normal size, and the washer 31 comes off the rod, so that the capsules separate and the lower one commences to release its contents.

Figure 7:
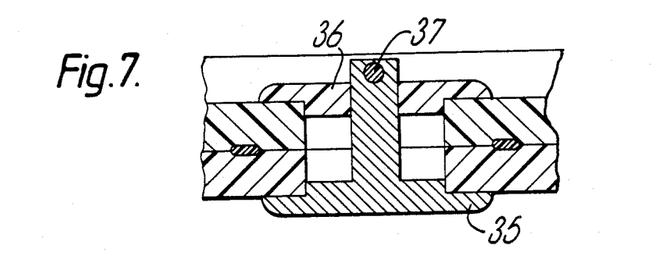

In FIG. 7 one washer 35, in this case the lower one, has a shank which fits through a hole in the other washer 36, the two washers being held together as shown by a CRG rod or tube 37. When the rod or tube 37 is dissolved, the washer 35, which is under tension against the capsule base, is released and comes off. Hence the upper capsule also comes off, and releases the material in the lower capsule. Here, as in all the other arrangements described herein, the pieces of capsule, etc., which come off leave the animal in the usual way, i.e. by regurgitation or in the faeces.

Figure 8:
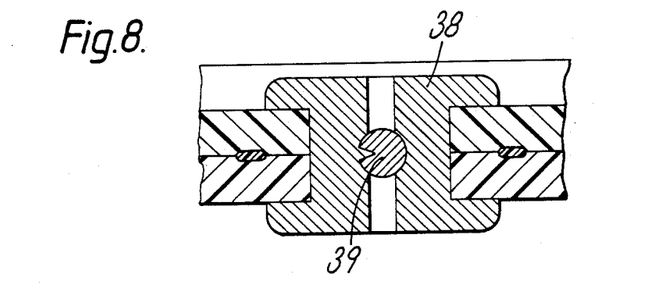

FIG. 8 shows two capsules held together by a grommet 38 with a CRG ball 39 in the middle. This ball is held in place by a recess on one side of the central shaft of the grommet, and a spike on the other side. When the CRG rod has dissolved sufficiently, the grommet collapses inwardly and releases the capsules from each other.

Figure 9:
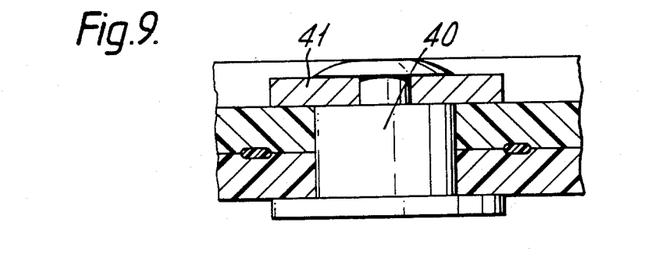

In the arrangement of FIG. 9 the capsules are held together by a stud 40 of a suitable plastics material, with a portion of reduced cross section at one end forced through a hole in a CRG disc 41. Hence when the CRG has dissolved sufficiently, the stud no longer effectively holds the capsules together so they separate to release the material in the lower capsule.

Figures 10, 11, 12:
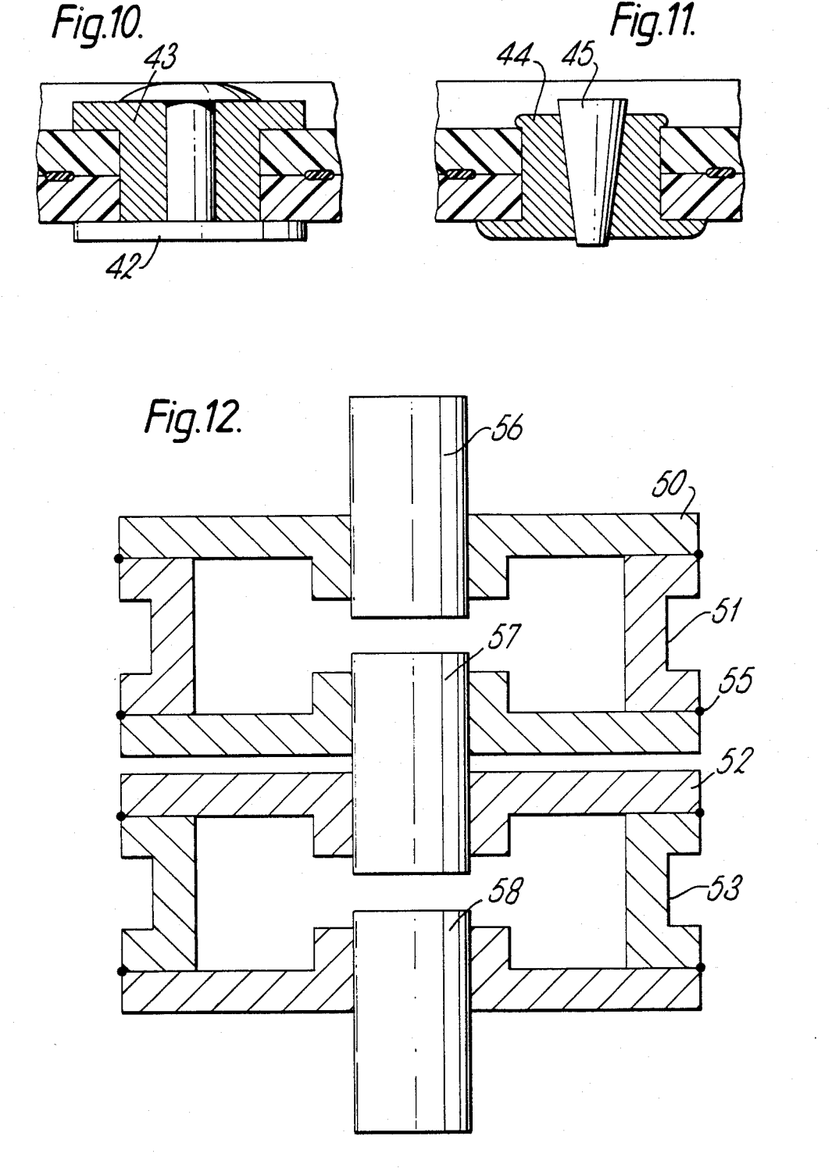
FIG. 12 is a dispenser assembly in which the contents of several receptacles can be released sequentially.

In FIG. 10 we see a stud 42 of plastics material which co-operates with a ferrule 43 of CRG. When the CRG has dissolved sufficiently, the capsules separate since the upper end of the stud is smaller in diameter than the holes in the capsule.

In FIG. 11 we see a stud 44 whose upper end is "splayed" over the surface of the upper capsule's base portion, and a frusto-conical CRG member 45. When the CRG has dissolved sufficiently, the stud 44 collapses to release the upper capsule so that the capsules separate, thus releasing the material in the lower capsule.

In all of the above arrangements the preferred materials for most of the components—except the CRG portions—are a suitable non-toxic plastics material. However, in some cases metallic components may be used, especially when the dispensing arrangement is used other than inside a living creature.

FIG. 12 shows another multi-capsule stack which includes a number of capsule sections 50, 51, 52, 53 . . . , fitted together by seam welds such as 55 in a multi-compartment stack. Each compartment has a filling of a material to be dispensed, and there are CRG rods 56, 57 and 58 each between two compartments. Thus when rod 56 dissolves, the material in the upper-most compartment is released, so that the fluid into which it is released reaches rod 57. This in its turn dissolves to release the material in the next compartment, and so on.

Figure 13:
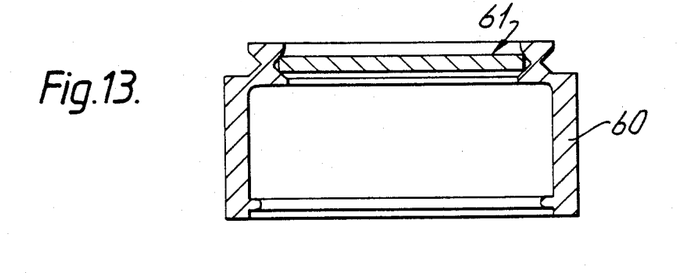
FIGS. 13 to 16 show alternative forms of dispenser intended for assembly for sequential release.

FIG. 13 shows another capsule which is basically an open-ended cylinder 60 with the upper end formed to snap-fit into the lower end of another cylinder. A disc 61 of a CRG is moulded or otherwise fitted into the upper end. When this is dissolved, the material in the capsule is released, and the disc of the next capsule comes under the influence of the fluid. When this disc dissolves, release of the next lot of material occurs, and so on. The bottom-most capsule has a closure which is not soluble in the "ambient" fluid.

Figure 14:
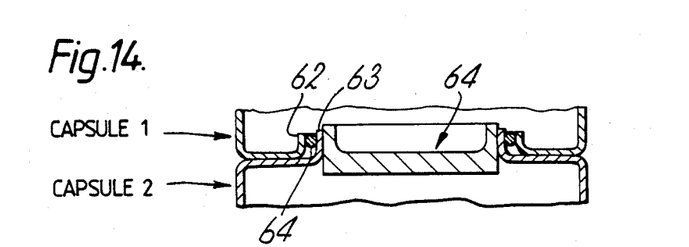

FIG. 14 shows another way of fitting adjacent capsules together. Here the two capsules have up-standing rims 62, 63, separated by an O ring 64. A CRG disc 64, with a cylindrical rim is pressure fitted inside the inner rim 63, thus holding the two capsules together. When the disc 64 has been dissolved, the material in the lower capsule is released. In addition, the absence of outwardly directed pressure from the disc 64 may allow the capsules to separate.

Figure 15:
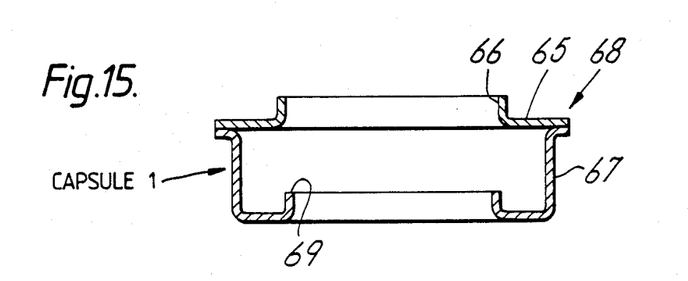

FIG. 15 shows a capsule with an upper disc-like portion 65 with an upstanding rim 66, secured to a lower cylindrical portion 67 by a weld seal 68. This cylindrical portion has an inwardly-extending rim 69. To fit two such capsules together, the rim 69 of one is fitted into a similar rim of another capsule with an O ring between the rims, and with a CRG disc inside the rim 69, in a manner similar to that described for the device of FIG. 14.

Figure 16:
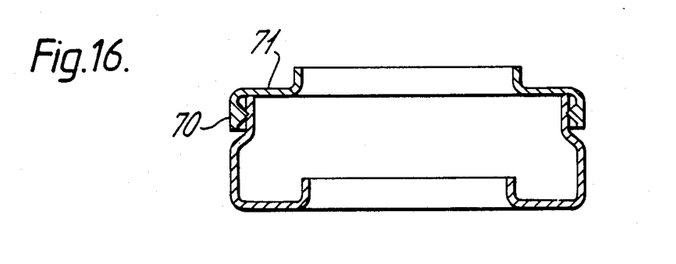

FIG. 16 has a downwardly-extending rim 70 on the uppermost portion 71, fitted in snap-action manner to the portion 72. Here the two portions have rims similar to those of the portions of the device shown in FIG. 15, and the capsules are fitted together in the way described with reference to FIG. 15.

Figure 17:
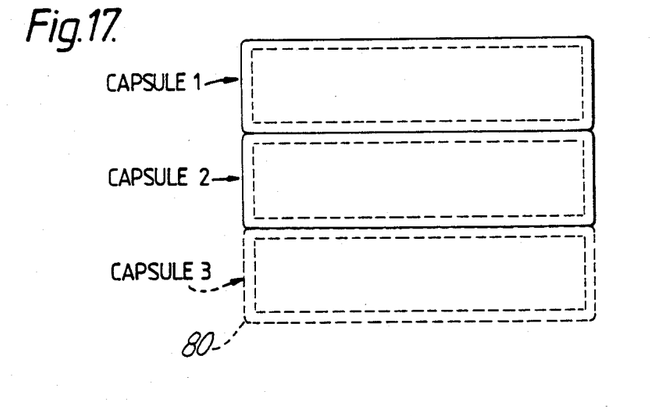
FIG. 17 is a multi-dispenser pack for sequential release.

FIG. 17 is a general view of three capsules which could be of the type shown in FIGS. 13 to 16, the capsules being made of suitable polymer materials, and secured together if necessary by welds as at 80. Thus in this case as the CRG discs are used up, the empty capsules do not fall off one after the other.

Figure 18:
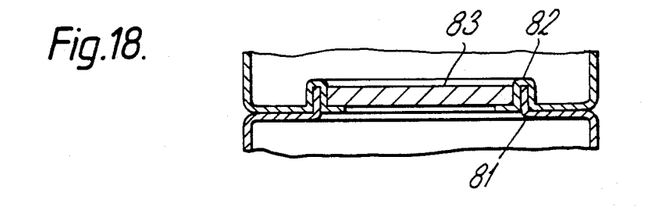
FIGS. 18 to 20 show different ways of securing together the individual dispensers of a multi-dispenser pack.

FIG. 18 shows another way of fitting two capsules together; here one has an upstanding rim 81 received by a U-shaped annulus 82 on the other, with the CRG disc 83 pressure fitted in the middle.

Figure 19:
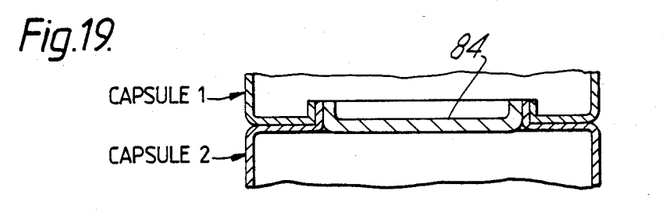
Figure 20:
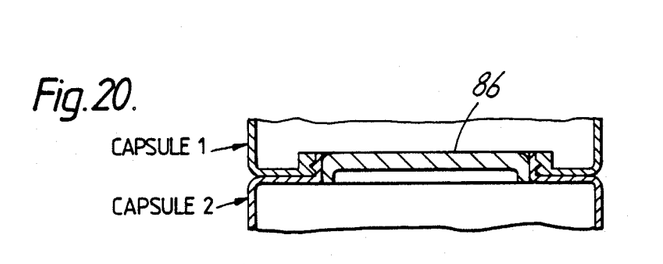

FIG. 19 has adjacent rims secured together, with the CRG disc 84 in the middle, while in FIG. 20 the rims fit together in snap-action manner, again with the CRG disc 86 in the middle.

Although we have described the dispensers as used for rumen boluses in ruminants, they have a wide range of other applications where material has to be dispensed accurately at known intervals.

In some arrangements described above we have shown circular containers; the ones actually shown are right circular cylindrical containers.

TABLE 1

| | BATCH WEIGHTS (g) | | | | | | | |
|---|---|---|---|---|---|---|---|---|
| | $NaH_2PO_4$ | $CaHPO_4$ | $KH_2PO_4$ | $Na_2CO_3$ | $3MgCO_3Mg(OH)_2.3H_2O$ | $P_2O_5$ | CALGON | $Zn_3(PO_4)_2.3H_2O$ |
| 1 | 32.4 | 12.2 | — | — | 3.2 | 9.0 | — | — |
| 2 | 24.0 | — | — | — | — | 18.0 | — | 19.2 |
| 3 | 55.8 | — | 0.7 | 3.2 | — | — | — | — |
| 4 | 42.0 | 6.8 | — | 3.7 | 3.2 | 1.5 | — | — |

TABLE 1-continued

| | BATCH WEIGHTS (g) | | | | | | |
|---|---|---|---|---|---|---|---|
| $NaH_2PO_4$ | $CaHPO_4$ | $KH_2PO_4$ | $Na_2CO_3$ | $3MgCO_3Mg(OH)_2 \cdot 3H_2O$ | $P_2O_5$ | CALGON | $Zn_3(PO_4)_2 \cdot 3H_2O$ |
| 5 — | 6.8 | — | 2.0 | — | — | 44.0 | — |

TABLE 2

| | MOLE % | | | | | | | TIME TO DISSOLVE THROUGH 5 mm Plate | | | |
|---|---|---|---|---|---|---|---|---|---|---|---|
| | $Na_2O$ | $Ka_2O$ | CaO | MgO | ZnO | $P_2O_5$ | SOLUTION RATE cm/d, | Conditions | yr | days | hrs | mins |
| 1 | 53.5 | 0.5 | — | — | — | 46.0 | 10.0 tap water, | 25° C., Static | — | — | 1 | 10 |
| 2 | 44.7 | — | 9.5 | — | — | 45.8 | 0.13 " | 10° C., flowing | — | 3 | 20 | — |
| 3 | 43.0 | — | 10.2 | 7.2 | — | 39.6 | 0.04 dist. water, | 38° C., flowing | — | 12 | 12 | — |
| 4 | 27.1 | — | 18.0 | 7.0 | — | 47.9 | 0.0013 " | " | 1 | 20 | — | — |
| 5 | 20.1 | — | — | — | 27.1 | 52.5 | 0.005 " | " | — | 100 | — | — |

However, these cylindrical containers could have a variety of different cross-sections other than circular. Thus, for example, square of hexangular cross-sections could also be used.

The above dispensers are made in the main from relatively cheap non-toxic plastics material, for instance using injection moulding. The CRG members used to control the time of release are small compared with the whole dispenser, so that although they are precision components made to close tolerances they are relatively cheap. To give an indication of relative sizes, the overall diameter of the multiple dispenser shown in FIG. 1 is 30 mm, and its CRG rod is about 13 mm long and 1.5 mm thick. The dimensions of the other dispensers are comparable to those of the single dispenser portions of the FIGS. 1-2 arrangement.

We claim:

1. A dispenser for dispensing material into a fluid medium, which dispenser when in use is located in the fluid medium into which the material is to be dispensed, wherein:
   the dispenser includes a container of a plastics material or metal for the material to be dispensed;
   a closure of a rubber or plastics material for the container is provided;
   a retainer holds the closure in place, which retainer is made of a controlled release glass (CRG) material, which CRG material is a plural oxide material soluble in the fluid medium into which the material is to be dispensed;
   when in use the dispenser is immersed in said fluid medium so that the CRG is subjected to the dissolving action of the fluid medium, whereby said CRG material dissolves in the fluid medium to cause the retainer to be rendered ineffective after a period dependent on the characteristics of the CRG retainer, so that the closure is released to cause the material therein to be released into the fluid medium.

2. A dispenser as claimed in claim 1, wherein:
   the container is generally cylindrical with a bevel on its inner surface;
   the closure is a ball of a rubber or plastics material located in the container by the bevel; and
   the ball is held in place in the container by a rod or tube of said CRG material forming the retainer and extending transversely across the container on the outside of the ball.

3. A dispenser as claimed in claim 1, herein:
   the container is generally cylindrical with a bevel on the inner surface of the container;
   the closure is a ball of a rubber or plastics material located in the container by the bevel; and
   the ball is held in place in the container by a disc of said CRG material forming the retainer, which disc is received in recesses in the inner wall of the container and extends across the container on the outside of the ball.

4. An arrangement as claimed in claim 1, wherein the retainer is a plug of a controlled release glass (CRG) material in the closure.

5. A multi-dispenser assembly, which includes a cylindrical member with a number of holes each of which forms the container for a single dispenser as claimed in claim 4.

6. A dispenser as claimed in claim 4, wherein the functions of the closure and of the retainer are combined in a single member of CRG.

7. A dispenser arrangement for dispensing material into a fluid medium, which dispenser arrangement when in use is located in the fluid medium into which the material is to be dispensed, where:
   the arrangement includes a stack of individual dispensers each of which is a container with an end face having one or more holes via which the material therein can escape into a said fluid medium, each said container being made of a plastics material or metal;
   said dispensers are secured together to form a stacked array of said dispensers;
   each said dispenser is secured to its neighbour in the stack by a fastening including a member of controllable release glass (CRG), which CRG is a plural oxide material, so that the first dispenser forms a closure member for the next dispenser in the stack and so on;
   wherein when the material is released from the first dispenser said release causes the member of CRG between that dispenser and the second dispenser to be dissolved by the fluid medium; and
   wherein when said CRG member is dissolved the first dispenser is detached from the second dispenser so that the material in the second dispenser is released to the fluid medium, a similar process of sequential release continuing for any further dispensers.

8. An arrangment as claimed in claim 7, wherein each said dispenser has a small hole in its other end face which receives an upstanding lug with a hole in it, wherein to assemble two said dispensers together the lug in one is fitted into the small hole in the other end face of the other dispenser and a CRG rod or tube fitted through the hole in the lug so as to secure the dispensers together.

9. An arrangement as claimed in claim 7, wherein each said dispenser has a small central hole in each said end face, wherein to secure two dispensers together securing means interconnects said two small holes, and wherein said securing means includes a CRG member which when dissolved releases the securing means.

10. An arrangment as claimed in claim 7, wherein each said dispenser consists of a base member of plastics material and a cap member also of plastics material, which fit together in a snap-action manner.

* * * * *